(12) United States Patent
Shulko

(10) Patent No.: US 10,960,226 B1
(45) Date of Patent: Mar. 30, 2021

(54) EYE PROTECTOR FOR USE WITH IMMOBILIZATION MASKS DURING RADIOTHERAPY

(71) Applicant: Gail Shulko, Hopewell, OH (US)

(72) Inventor: Gail Shulko, Hopewell, OH (US)

( * ) Notice: Subject to any disclaimer, the term of this patent is extended or adjusted under 35 U.S.C. 154(b) by 0 days.

(21) Appl. No.: 17/120,561

(22) Filed: Dec. 14, 2020

(51) Int. Cl.
*A61N 5/10* (2006.01)
*A61F 9/04* (2006.01)

(52) U.S. Cl.
CPC .............. *A61N 5/10* (2013.01); *A61F 9/045* (2013.01); *A61N 2005/1094* (2013.01); *A61N 2005/1096* (2013.01); *A61N 2005/1097* (2013.01)

(58) Field of Classification Search
None
See application file for complete search history.

(56) References Cited

U.S. PATENT DOCUMENTS

| | | | | |
|---|---|---|---|---|
| 4,550,713 A * | 11/1985 | Hyman | ................... | A61F 9/007 128/849 |
| 7,748,387 B1 * | 7/2010 | Vu | ........................... | A61F 9/04 128/858 |
| 2014/0330417 A1 * | 11/2014 | Keane | ................... | A61B 90/18 700/98 |
| 2015/0000674 A1 * | 1/2015 | Barthe | ..................... | A61B 8/44 128/847 |
| 2018/0192971 A1 * | 7/2018 | Ballsieper | ................ | A61N 5/10 |
| 2018/0296852 A1 * | 10/2018 | Tapper | ................. | A61N 5/0616 |
| 2019/0216639 A1 * | 7/2019 | Bruder | ...................... | A61F 7/02 |
| 2019/0366030 A1 * | 12/2019 | Giap | ...................... | G16H 40/63 |

* cited by examiner

*Primary Examiner* — Hoon K Song
(74) *Attorney, Agent, or Firm* — Aaron P. McGushion

(57) ABSTRACT

The present specification discloses a radiation therapy protective eye mask for covering a patient's eyes, with the radiation therapy protective eye mask being placed over the eyes and beneath an immobilization mask. The radiation therapy protective eye mask includes a radiation shielding layer configured to cover at least one eye when a patient is undergoing radiotherapy treatments. A first layer of material can be positioned between the radiation shielding layer and the eyes, to provide cushioning and barrier between the radiation shielding layer and the skin. The radiation therapy protective eye mask can include a concave portion over the eyes to permit opening and closing of the eyes. Further radiation shielding layer can include structural and/or surface features and contours to reflect at least some of the radiation. In this way, the present eye protector reduces the quantity of radiation incident on the eyes for reducing eye damage.

20 Claims, 4 Drawing Sheets

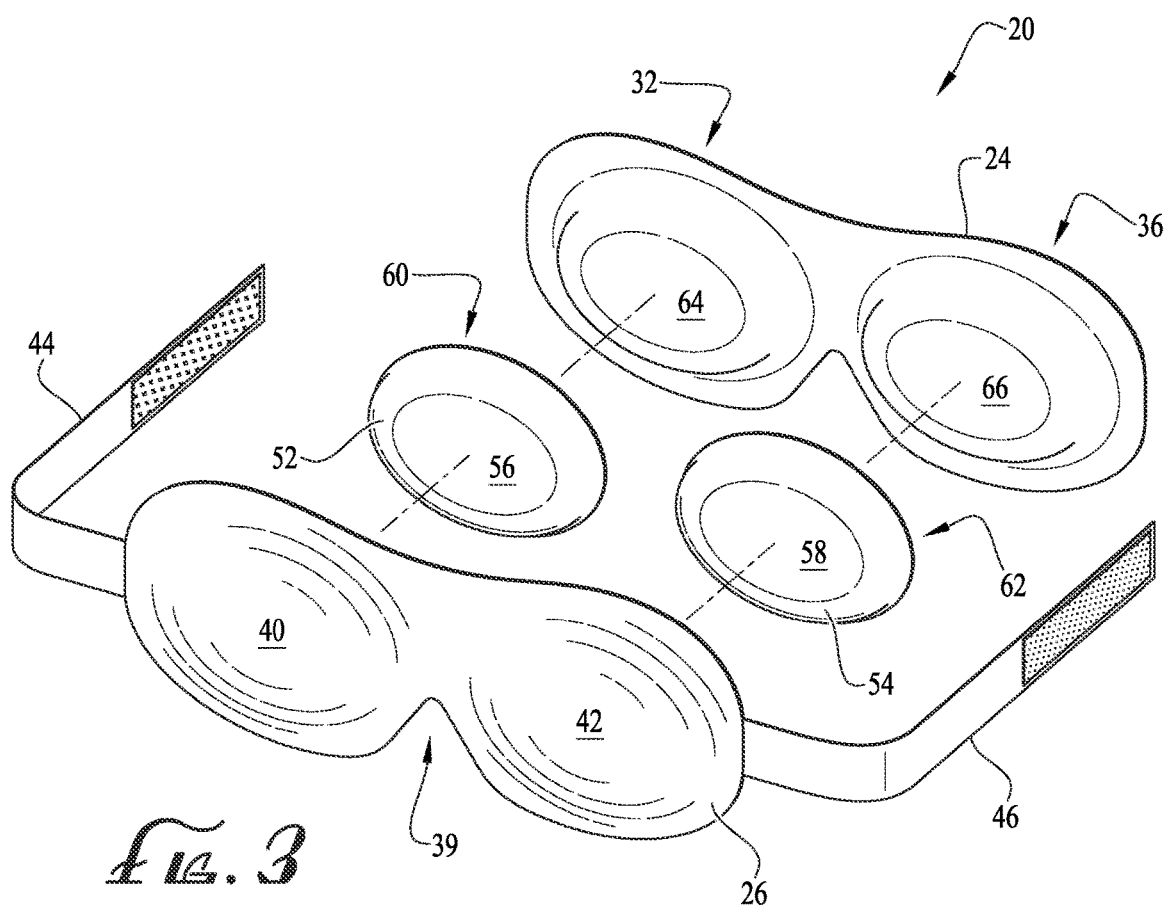
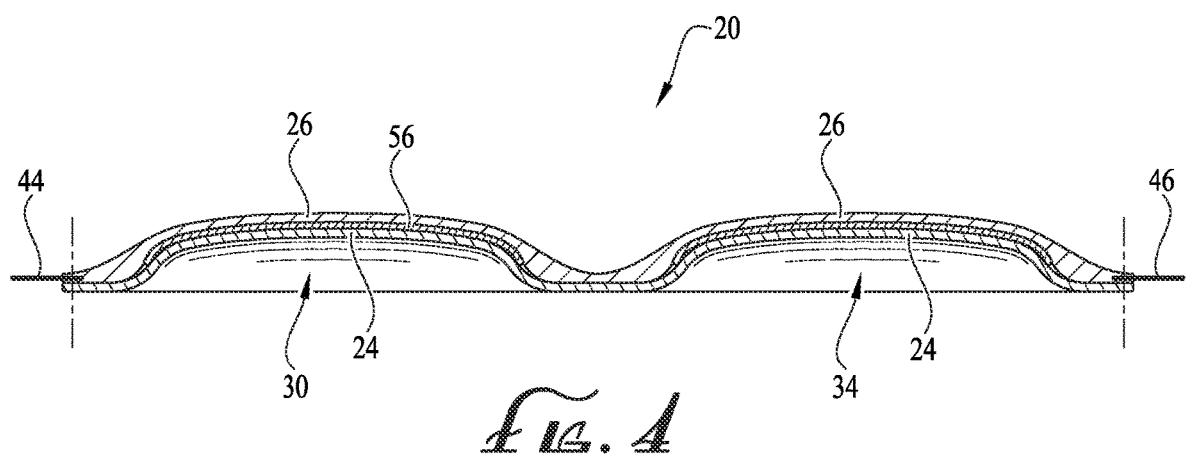

US 10,960,226 B1

EYE PROTECTOR FOR USE WITH IMMOBILIZATION MASKS DURING RADIOTHERAPY

BACKGROUND

The subject of this patent application relates generally to personal protective equipment for use by patients in radiotherapy.

By way of background, in certain cancer treatments such as brain, throat, mouth and thyroid cancers, the patient's head is immobilized using an immobilization mask. An immobilization mask is commonly a thermoplastic mesh sheet that is heated and stretched over the patient's head and optionally over the shoulders and the torso of the patient, and conformed to the contours of the head and body. Once cooled, the immobilization mask hardens and maintains its shape for future treatment. During radiotherapy, the immobilization mask is placed over the head to prevent movement of the patient's head and upper body during the treatment. In this way, radiation can be emitted to a focused region for treatment of the disease.

Unfortunately, the patient receives large doses of radiation to the head region, and especially to the eyes. The levels of radiation commonly incident on the eyes during a course of treatment is sufficient to cause significant damage to the eyes, requiring further treatment after an already trying time. A protective means is needed to prevent excessive exposure to radiation to the eyes, without interfering with the function of the immobilization mask.

Aspects of the present invention fulfill these needs and provide further related advantages as described in the following summary.

SUMMARY

Aspects of the present invention teach certain benefits in construction and use which give rise to the exemplary advantages described below.

The present specification discloses a radiation therapy protective eye mask for covering a patient's eyes, with the radiation therapy protective eye mask being placed over the eyes and beneath an immobilization mask. The radiation therapy protective eye mask includes a radiation shielding layer configured to cover at least one eye when a patient is undergoing radiotherapy treatments. A first layer of material can be positioned between the radiation shielding layer and the eyes, to provide cushioning and barrier between the radiation shielding layer and the skin. The radiation therapy protective eye mask can include a concave portion over the eyes to permit opening and closing of the eyes. Further radiation shielding layer can include structural and/or surface features and contours to reflect at least some of the radiation. In this way, the present eye protector reduces the quantity of radiation incident on the eyes; for reducing, eye damage.

Other features and advantages of aspects of the present invention will become apparent from the following more detailed description, taken in conjunction with the accompanying drawings, which illustrate, by way of example, the principles of aspects of the invention.

BRIEF DESCRIPTION OF THE DRAWINGS

The accompanying drawings illustrate aspects of the present invention. In such drawings:

FIG. 3 is an exploded front perspective view of the photobiomodulation therapy garment of FIG. 1;

FIG. 4 is a cross sectional view of the radiation therapy protective eye mask of FIG. 1;

Figure 1:
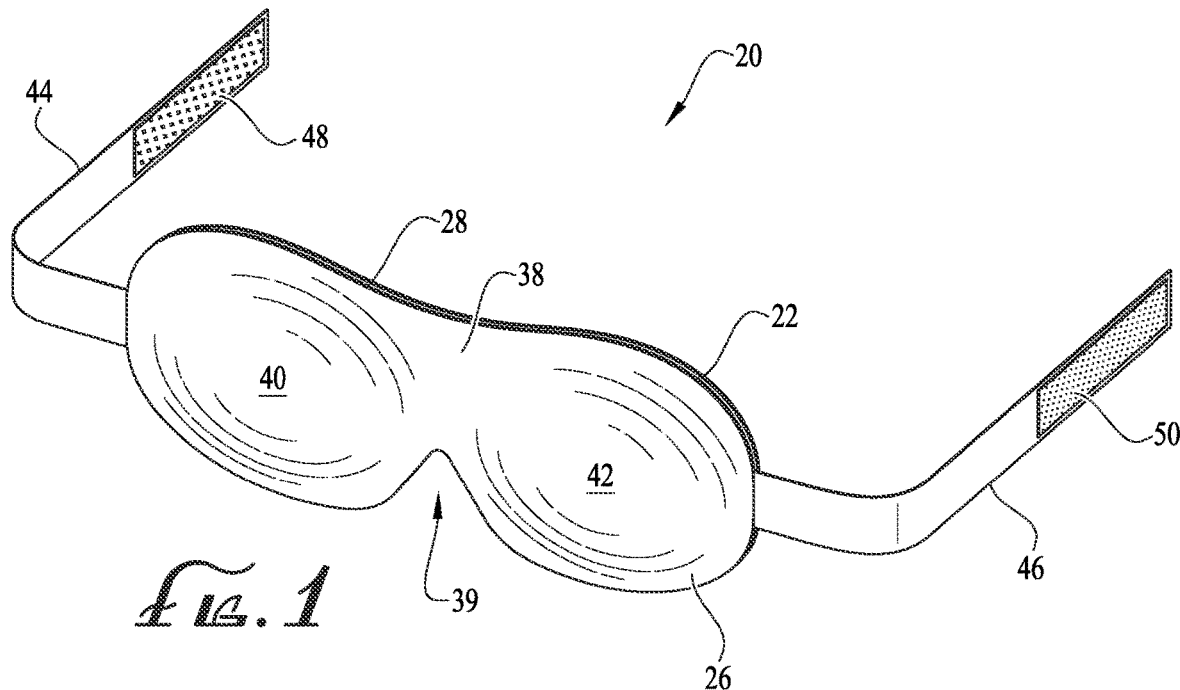
FIG. 1 is a front perspective view of an exemplary embodiment of the present radiation therapy protective eye mask.
Figure 2:
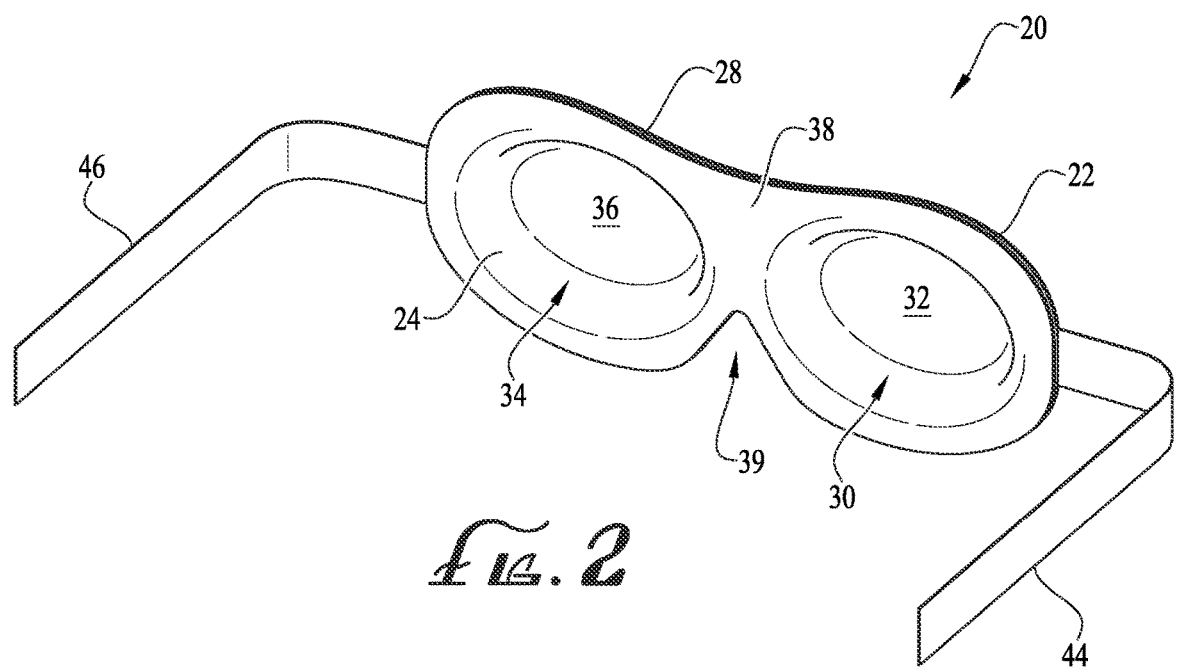
FIG. 2 is a back perspective view of the radiation therapy protective eye mask of FIG. 1.

The above described drawing figures illustrate aspects of the invention in at least one of its exemplary embodiments, which are further defined in detail in the following description. Features, elements, and aspects of the invention that are referenced by the same numerals in different figures represent the same, equivalent, or similar features, elements, or aspects, in accordance with one or more embodiments.

DETAILED DESCRIPTION

The detailed descriptions set forth below in connection with the appended drawings are intended as a description of embodiments of the invention, and is not intended to represent the only forms in which the present invention may be constructed and/or utilized. The descriptions set forth the structure and the sequence of steps for constructing and operating the invention in connection with the illustrated embodiments. It is to be understood, however, that the same or equivalent structures and steps may be accomplished by different embodiments that are also intended to be encompassed within the spirit and scope of the invention.

The present devices and methods in one or more embodiments provides a radiation therapy protective eye mask (which may also be referred herein as an eye protector) 20 for covering a patient's P eyes, with the eye protector 20 being placed over the eyes and beneath an immobilization mask 500. The eye protector 20 includes, at minimum, a second layer (which may also be referred herein as a radiation shielding layer, and may or may not necessarily be a layered arrangement) 52 and/or 54 covering at least one eye. In one or more embodiments, a first layer of material 24 is positioned between the eye and the radiation shielding layer 52, 54, and can provide a cushioning and protective layer between the patient's P skin about the eye region. In one or more embodiments, a third layer of material 26 situated atop the radiation shielding layer 52, 54 can be provided for enclosing the radiation shielding layer 52, 54 between the first layer of material 24 and the third layer of material 26. In one or more embodiments, the first layer of material 24 includes a concave portion 30, 34 that provides a clearance between the concave inner surface 32, 36 and the patient's P eyes, so that the eyes can function normally or near normally, adding to the patient's comfort and reducing stress. In one or more embodiments, the radiation shielding layer 52, 54 includes an outwardly facing surface 56, 58 that includes a surface contour that angles the surface 56, 58 so that much of the surface 56, 58 is directed at an oblique angle to the incident radiation so that at least some of the radiation is reflected away from the patient's P eye and some of the radiation will be absorbed and scattered by the radiation shielding layer 52, 54. In this way, the present eye protector 20 reduces the quantity of radiation incident on the eyes; and, as a result, eye damage is substantially reduced.

Example embodiments of the present eye protector 20 are illustrated in FIGS. 1-7. Looking first at FIGS. 1 and 2, an exemplary embodiment of the eye protector 20 is illustrated as an eye mask and generally includes a first layer of material 24 made of a pliable material which is comfortable against the skin, such as a textile, a foam, a quilted material, felt, or the like. In this example, the pliable material is a foam laminate. The first layer of material 24 is the layer closest to the skin, and can contact the skin in one or more portions about the eye, although contact with the skin is not required for operation of the radiation shielding layer 52, 54. The first layer of material 24 is molded to form the right concave portion 30 with a right concave inner surface 32 and a left concave portion 34 with a left concave inner surface 36. The right concave portion 30 provides relief for the right eye to reduce the amount of direct pressure on the eye at minimum or to provide enough clearance to blink the eye and have the eye open or closed comfortably. Similarly, the left concave portion 34 provides relief for the left eye. A flange 29 can optionally be formed about the right concave portion 30 and the left concave portion 34 with a nasal relief 39 formed between the portions 30, 34. The third layer of material 26 is positioned on top of the first layer of material 24 and configured to be positioned furthest from the eye. The first layer of material 24 and the third layer of material 26 can be made of the same material, such as the foam laminate material. The optional flange 29 on the first layer of material 24 and the third layer of material 26 provides a region to connect the first layer of material 24 to the third layer of material 26 about the perimeter edge 28 though sewing, gluing, heat sealing, or other appropriate attachment method. Bias tape can be used to cover the seam about the perimeter edge 28. Extending from the right side of the eye mask 20 is a right strap 44; and extending from the left side of the eye protector mask 20 is a left strap 46. The free ends of the straps 44, 46 are releasably fastened together using releasable fasteners, such as hook and loop pairs 48, 50. A nasal bridge portion 38 joins the right concave portion 30 and the left concave portion 34 and creates a gap between the two for accommodating a nose. Although the right concave portion 30 and the left concave portion 34 are shown as attached by the nasal bridge portion 38, this is an optional feature, and the two portions 30, 34 may be separate pieces, each placed over their respective eyes, with no straps 44, 46 required. Furthermore, the right strap 44 and the left strap 46 are optional with the nasal bridge portion 38 embodiment. The eye protector mask 20 may be placed atop the eyes without the straps 44, 46 and held in place by the immobilization mask 500.

In the illustrated example embodiment, the third layer of material 38 is made of a pliable fabric (e.g., a foam laminate or the like) having a right outermost surface 40 and a left outermost surface 42, which is configured to directly engage with and contact the immobilization mask 500 during radiation therapy. Here the outermost surfaces 40, 42 are generally convex, mainly due to their conforming to the shape of the radiation shielding layer 52, 54 below. However, the shape of the outermost surfaces 40, 42 of the third layer of material 26 can be configured to protrude so that, during the immobilization mask 500 fitting process, the immobilization mask 500 is molded to the shape (or approximate shape) of the outermost surfaces 40, 42. In this way, a negative of the protrusions (a convexity in this example) is formed in the immobilization mask 500 (at two areas in this example). So, when the immobilization mask 500 is placed over the eye protector mask 20 during a radio therapy session, the outermost surfaces 40, 42 will act as a key and register within the negative (depressions in this example) portions of the immobilization mask 500 so that the eye protector mask 20 will be properly positioned on the patient and within the immobilization mask 500. Of course, shapes other than dome-like shapes in the present example are possible on the outermost surfaces 40, 42 to produce the same registering effect, such as a protruding polyhedron. Further, alignment indicia can be marked or printed on both the eye protector mask 20 and the immobilization mask 500 so that the technician or other personnel can align one to the other, such as alignment lines, dots, or other markings that visually insure alignment between the eye protector mask 20 and the immobilization mask 500 to insure protection of the eyes and comfort for the patient.

As briefly described above, and also referring to FIGS. 3 and 4, the radiation shielding layer 52, 54 is positioned between the first layer of material 24 and the third layer of material 38, with the right second layer of material 52 positioned on the right outer surface 64 over the right concave portion 30 and the left second layer of material 54 positioned on the left outer surface 66 over the left concave portion 34. In one or more embodiments, the right inwardly facing surface 60 and the left inwardly facing surface 62 (visible in cross-section of FIG. 4) can be generally concave. Further, in one or more embodiments, the right outer surface 64 and the left outer surface 66 of the first layer of material 24 can be convex. The right inwardly facing surface 60 and the left inwardly facing surface 62 are positioned over the right outer surface 64 and the left outer surface 66 in a nested configuration to register the radiation shielding layer 52, 54 in place. Further the radiation shielding layer 52, 54 can be directly adhered or otherwise attached to the first layer of material 24 by gluing the right inwardly facing surface 60 and the left inwardly facing surface 62 to the right outer surface 64 and the left outer surface 66, respectively. In this way, the radiation shielding layer 52, 54 is fastened in place on the first layer of material 24. The third layer of material 26 is optional, but can be used to cover the radiation shielding layer 52, 54 for aesthetics, to further contain and protect the radiation shielding layer 52, 54, and to protect the user from contact with the radiation shielding layer 52, 54 (if the radiation shielding material is lead or other material not suitable for contact by a human).

The radiation shielding layer 52, 54 is made of a high atomic number material or high-Z materials, such as lead, aluminum, titanium, copper, etc. In one or more embodiments, a lead sheet material is used as the radiation shielding layer 52, 54, as it is inexpensive, easy to shape, and effective at reducing the radiation incident on the eyes therebelow. The thickness of the lead sheet material should be sufficient to reduce radiation exposure to the eyes to a less harmful or harmless level for a given dosimetry. In one or more embodiments, the lead sheet is greater than 0.050" thick, or is greater than 0.070" thick, or is greater than 0.090" thick, or is greater than 0.100" thick, or is greater than 0.120" thick, or is greater than 0.150" thick. Each high-Z material may have differing thickness to effectively reduce radiation exposure to the eyes. In one or more embodiments, the radiation shielding layer 52, 54 is made of lead sheet material formed into a cupped shape, where the resulting shape and sheet thickness of the radiation shielding layer 52, 54 is sufficiently strong to prevent collapse of the concave right inwardly facing surface 60 and the concave left inwardly facing surface 62 as the immobilization mask 500 is being fitted over the patient's P head H.

Figure 5:
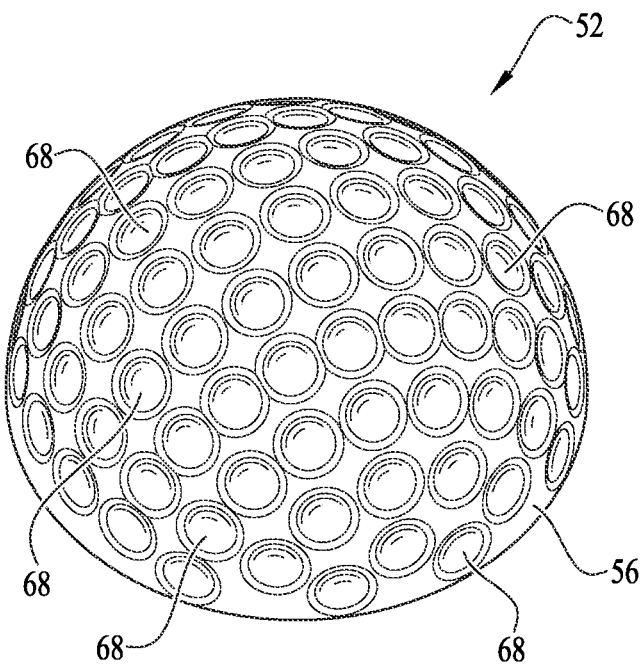
FIG. 5 is a top perspective view of an example embodiment of the radiation shielding layer, illustrating an example surface contour including a plurality of dimples.
Figure 6:
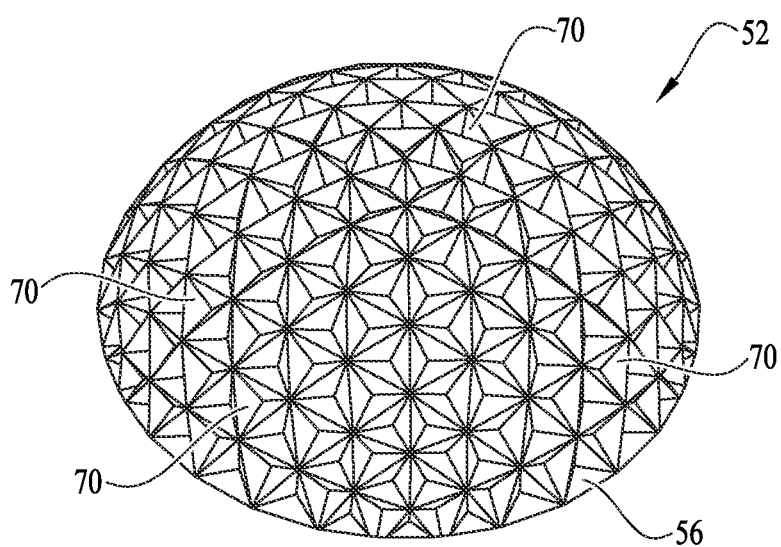
FIG. 6 is a top perspective view of an example embodiment of the radiation shielding layer, illustrating an example surface contour including a plurality of concave polyhedrons.

Referring now to FIGS. 5 and 6, two example embodiments of the radiation shielding layer 52 is illustrated (showing just the right side for simplicity, although the left side may look substantially the same or a mirror of the right side). The outwardly facing surface 56 of the radiation shielding layer 52 includes a surface contour (e.g., an overall outer shape, an imprinted shape, etc.), where the contour is configured to be directed obliquely to incident radiation when donned such that at least some of the radiation is reflected away from the patient's eye. The surface contour can be an imprinted design on constant or varying shapes, such as a plurality of dimples 68 and/or a plurality of concave polyhedrons 70, and or other various shapes known to reflect incident radio waves away from the object, such as angled surfaces, dihedral forms and reentrant triangles, etc. This surface contour can cover all, a majority, or a portion of the outwardly facing surface 56; or the surface contour can cover more than 20% of the outwardly facing surface 56, or more than 20% of the outwardly facing surface 56, or more than 30% of the outwardly facing surface 56, or more than 40% of the outwardly facing surface 56, or more than 50% of the outwardly facing surface 56, or more than 60% of the outwardly facing surface 56, or more than 70% of the outwardly facing surface 56, or more than 80% of the outwardly facing surface 56, or more than 90% of the outwardly facing surface 56.

The present eye protector mask 20 can be placed atop the eyes with or without straps. In this example embodiment, the eye protector mask 20 is separate from the immobilization mask 500. In another example embodiment, the eye protector mask 20 can be attached in situ to the immobilization mask 500, so that the eye protector mask 20 is permanently or detachably coupled to the immobilization mask 500, and would be correctly positioned so that the eye protector mask 20 covers the eyes when the immobilization mask 500 is placed over the head during treatment. The eye protector mask 20 can be clipped to, adhered to, intermeshed with, or otherwise attached to the immobilization mask 500. For example, one or more hook and loop fasteners can be placed on the right outermost surface 40 and/or the left outermost surface (or anywhere on the outermost surface or other appropriate portion of the eye protector mask 20), where the mating hook and loop fastener(s) is placed on the inside of the immobilization mask 500 for the purpose of detachably fastening the eye protector mask 20 to the immobilization mask 500.

Figure 7:
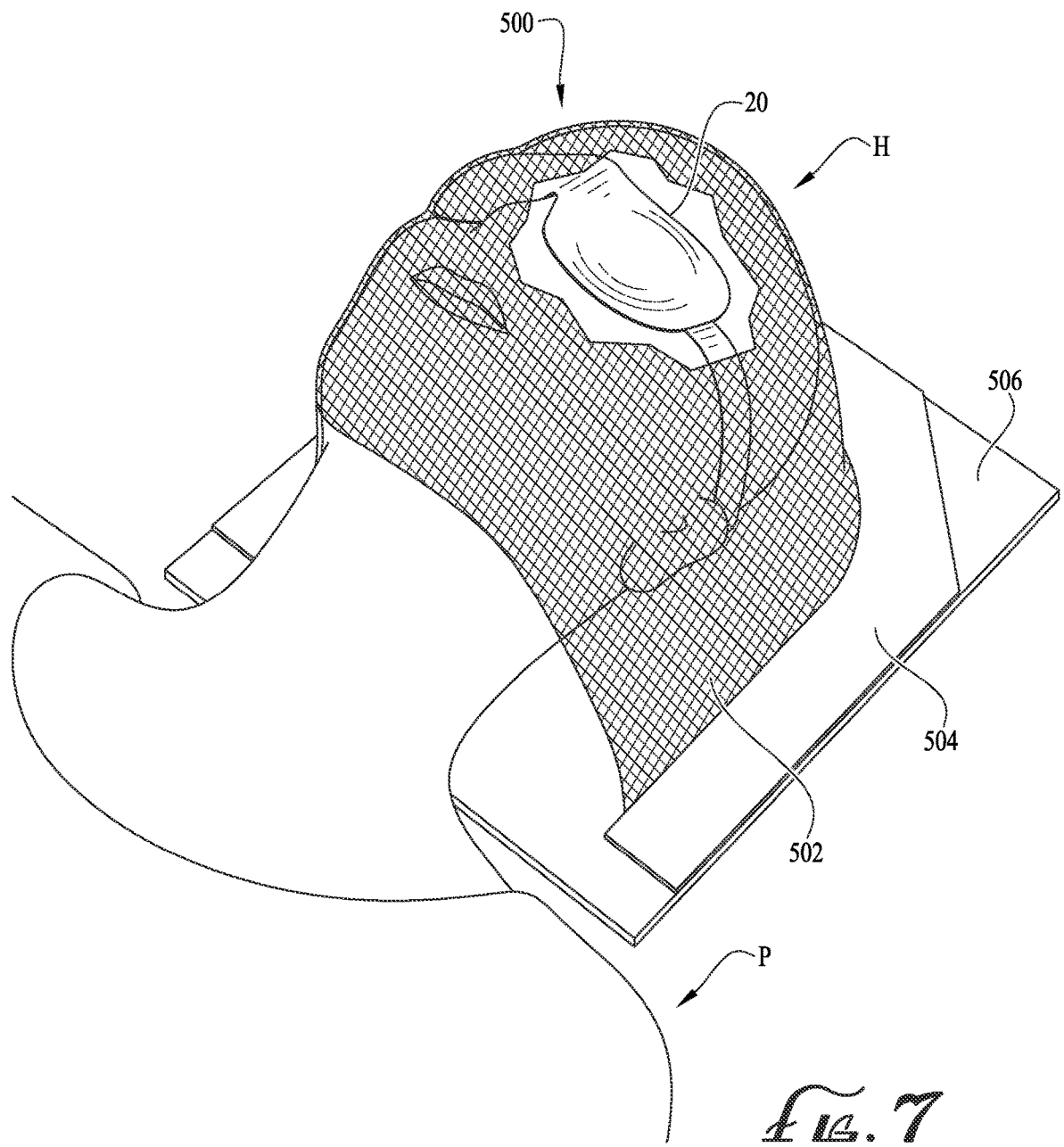
FIG. 7 is a top perspective view of the radiation therapy protective eye mask of FIG. 1, illustrating the radiation therapy protective eye mask donned on the patient while a radiation mask is being fitted.

FIG. 7 illustrates an example embodiment of the eye protector mask 20 placed over the patient's eyes and underneath the immobilization mask 500, with a portion of the immobilization mask 500 broken away so that the left portion of the eye protector mask 20 can be more clearly seen. Here, the head H is immobilized as the patient P undergoes radiotherapy. The radiation shielding layer 52, 54 are each positioned over the right and left eyes, respectively, and preventing at least some of the radiation from reaching the eyes.

Looking at an example method of fitting and using the present eye protector mask 20, the immobilization mask 500 (initially flat and is supported by a frame 506) is heated to soften the mesh 502. The eye protector mask 20 is placed on the patient's head H covering the eyes as described above. Fastening the straps 44, 46 is optional, but may be recommended if they are present. While still warm and plastic, the immobilization mask 500 is placed over the head H with the softened mesh portion 502 positioned over the face, and stretched over the face by pulling the frame 504 downwards to the table 506. The mesh portion 502 is then, both manually and as part of the stretching, conformed to various features of the face and, optionally, to the outermost surfaces 40, 42 of the eye protector mask 20. The frame 504 is locked in place to the table 506, where the patient P awaits for the mesh portion to sufficiently harden so that the mesh portion 502 maintains its molded shape when removed.

Aspects of the present specification may also be described as follows:

1. An eye protector for use with an immobilization mask during radiation therapy to reduce radiation exposure to a patient's eye, the eye protector including a first layer of a compliant material with a concave portion having a concave inner surface and an outer surface opposing the concave inner surface, the concave portion configured to enclose the patient's eye and provide a clearance for the patient's eye when the compliant material is donned atop the patient's eye; and a second layer of a radiation shielding material joined with the first layer and positioned atop the outer surface and substantially covering the concave portion, the radiation shielding material having an inwardly facing surface directed toward the outer surface and an outwardly facing surface directed away from the inwardly facing surface, a majority of the outwardly facing surface having a surface contour configured to be directed obliquely to incident radiation when donned such that at least some of the radiation is reflected away from the patient's eye; where the first layer and the second layer are configured to be donned between the patient's eye and the immobilization mask.

2. The eye protector of embodiment 1 wherein the surface contour includes one or both of a plurality of dimples and a plurality of concave polyhedrons.

3. The eye protector of embodiments 1 or 2 further comprising a third layer of material positioned atop the second layer, the second layer being sandwiched between the first layer and the third layer.

4. The eye protector of any one of embodiments 1-3 wherein the third layer of material is fastened about a perimeter to the second layer enclosing the second layer therebetween.

5. The eye protector of any one of embodiments 1-4 wherein the first layer and the third layer of material are each made of a foam laminate material.

6. The eye protector of any one of embodiments 1-5 wherein the first layer and the second layer form a right side configured to cover a patient's right eye when donned, a left side is substantially duplicative of the right side construction and is configured to cover a patient's left eye when donned.

7. The eye protector of any one of embodiments 1-6 wherein the right side is connected to the left side and is configured to simultaneously cover the patient's right eye and the patient's left eye.

8. The eye protector of any one of embodiments 1-7 further comprising a strap connecting the right side and the left side and is configured to wrap about a patient's head when donned.

9. The eye protector of any one of embodiments 1-8 wherein the first layer and the second layer form an assembly, the assembly is configured to be sufficiently stiff to resist substantial collapse of the clearance as the immobilization mask is molded about a patient's head, so that the patient's eye can open and close without substantial hindrance caused by contact with the concave inner surface.

10. An eye protector for use with an immobilization mask during radiation therapy to reduce radiation exposure to a patient's right eye and a patient's left eye, the eye protector including a first layer with a right portion and a left portion, the right portion having a right inner surface and a right outer surface opposing the right inner surface, the left portion having a left inner surface and a left outer surface opposing the left inner surface, the right portion of the first layer configured to substantially cover and to be positioned closest to the patient's right eye and the left portion of the first layer configured to substantially cover and to be positioned closest to the patient's left eye; and a second layer of a radiation shielding material joined with the first layer and positioned atop the outer surface and substantially covering the concave portion, the radiation shielding material having an inwardly facing surface directed toward the outer surface and an outwardly facing surface directed away from the inwardly facing surface; and an assembly comprising the first layer and the second layer, the assembly being configured to be donned between the patient's eye and the immobilization mask and configured to be sufficiently stiff to resist substantial collapse of the right portion and the left portion as the immobilization mask is molded about a patient's head.

11. The eye protector of embodiment 10 wherein a majority of the outwardly facing surface includes a surface contour configured to be directed obliquely to incident radiation when donned such that at least some of the radiation is reflected away from the patient's eye.

12. The eye protector of embodiments 10 or 11 wherein the surface contour includes one or both of a plurality of dimples and a plurality of concave polyhedrons.

13. The eye protector of any one of embodiments 10-12 wherein the right portion further includes a right concave portion and the right inner surface is concave and the left portion further includes a left concave portion and the left inner surface is concave.

14. The eye protector of any one of embodiments 10-13 further comprising a third layer of material positioned atop the second layer, the second layer being sandwiched between the first layer and the third layer, and the third layer of material is fastened about a perimeter to the second layer enclosing the second layer therebetween.

15. The eye protector of any one of embodiments 10-14 wherein the first layer and the third layer of material are each made of a foam laminate material.

16. The eye protector of any one of embodiments 10-15 further comprising a strap connecting the right side and the left side and is configured to wrap about a patient's head when donned.

17. The eye protector of any one of embodiments 10-16 wherein the first layer and the second layer form an assembly, the assembly is configured to be sufficiently stiff to resist substantial collapse as the immobilization mask is molded about a patient's head, so that the patient's eye can open and close without substantial hindrance caused by contact with the concave inner surface.

18. A method of fitting an immobilization mask, the method comprising the steps of providing an eye protector that includes a first layer of material with a concave portion having a concave inner surface and an outer surface opposing the concave inner surface, the concave portion configured to enclose the patient's eye and provide clearance for the patient's eye; and a second layer of a radiation shielding material positioned atop the outer surface of the first layer and substantially covering the concave portion, the radiation shielding material having an inwardly facing surface directed toward the outer surface and an outwardly facing surface directed away from the inwardly facing surface; positioning the eye protector atop a patient's eye so that each of the patient's eyes are substantially covered by the radiation shielding; applying the immobilization mask over a patient's head when the immobilization is in a softened state, with the eye protector positioned between the patient's eyes and the immobilization mask; molding the immobilization mask to conform to the eye protector when the immobilization is in the softened state; and curing the immobilization mask until sufficiently hardened.

19. The eye protector of embodiment 18 wherein the outwardly facing surface includes a surface contour configured to be directed obliquely to incident radiation when donned such that at least some of the radiation is reflected away from the patient's eye.

20. The eye protector of embodiment 18 or 19 wherein the surface contour includes one or both of a plurality of dimples and a plurality of concave polyhedrons.

In closing, it is to be understood that, although aspects of the present specification are highlighted by referring to specific embodiments, one skilled in the art will readily appreciate that these disclosed embodiments are only illustrative of the principles of the subject matter disclosed herein. The specific embodiments are not intended to be exhaustive or to limit the invention to the precise forms disclosed. Therefore, it should be understood that the disclosed subject matter is in no way limited to a particular compound, composition, article, apparatus, methodology, protocol, and/or reagent, etc., described herein, unless expressly stated as such. In addition, those of ordinary skill in the art will recognize that certain changes, modifications, permutations, alterations, additions, subtractions and sub-combinations thereof can be made in accordance with the teachings herein without departing from the spirit of the present specification. It is therefore intended that the scope of the invention is not to be limited by this detailed description. Furthermore, it is intended that the following appended claims and claims hereafter introduced are interpreted to include all such changes, modifications, permutations, alterations, additions, subtractions and sub-combinations as are within their true spirit and scope.

Certain embodiments of the present invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified, thus fulfilling the written description of all Markush groups used in the appended claims.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. For instance, as mass spectrometry instruments can vary slightly in determining the mass of a given analyte, the term "about" in the context of the mass of an ion or the mass/charge ratio of an ion refers to +/−0.50 atomic mass unit. At the very least, and not as an attempt to limit the application of the doctrine of equivalents to the scope of the claims, each numerical indication should at least be construed in light of the number of reported significant digits and by applying ordinary rounding techniques.

Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

Use of the terms "may" or "can" in reference to an embodiment or aspect of an embodiment also carries with it the alternative meaning of "may not" or "cannot." As such, if the present specification discloses that an embodiment or an aspect of an embodiment may be or can be included as part of the inventive subject matter, then the negative limitation or exclusionary proviso is also explicitly meant, meaning that an embodiment or an aspect of an embodiment may not be or cannot be included as part of the inventive subject matter. In a similar manner, use of the term "optionally" in reference to an embodiment or aspect of an embodiment means that such embodiment or aspect of the embodiment may be included as part of the inventive subject matter or may not be included as part of the inventive subject matter. Whether such a negative limitation or exclusionary proviso applies will be based on whether the negative limitation or exclusionary proviso is recited in the claimed subject matter.

The terms "a," "an," "the" and similar references used in the context of describing the present invention (especially in the context of the following claims) are to be construed to cover both the singular and the plural, unless otherwise indicated herein or clearly contradicted by context. Further, ordinal indicators—such as, e.g., "first," "second," "third," etc.—for identified elements are used to distinguish between the elements, and do not indicate or imply a required or limited number of such elements, and do not indicate a particular position or order of such elements unless otherwise specifically stated. All methods described herein can be performed in any suitable order unless otherwise indicated herein or otherwise clearly contradicted by context. The use of any and all examples or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

When used in the claims, whether as filed or added per amendment, the open-ended transitional term "comprising", variations thereof such as, e.g., "comprise" and "comprises", and equivalent open-ended transitional phrases thereof like "including," "containing" and "having", encompass all the expressly recited elements, limitations, steps, integers, and/or features alone or in combination with unrecited subject matter; the named elements, limitations, steps, integers, and/or features are essential, but other unnamed elements, limitations, steps, integers, and/or features may be added and still form a construct within the scope of the claim. Specific embodiments disclosed herein may be further limited in the claims using the closed-ended transitional phrases "consisting of" or "consisting essentially of" (or variations thereof such as, e.g., "consist of", "consists of", "consist essentially of", and "consists essentially of") in lieu of or as an amendment for "comprising." When used in the claims, whether as filed or added per amendment, the closed-ended transitional phrase "consisting of" excludes any element, limitation, step, integer, or feature not expressly recited in the claims. The closed-ended transitional phrase "consisting essentially of" limits the scope of a claim to the expressly recited elements, limitations, steps, integers, and/or features and any other elements, limitations, steps, integers, and/or features that do not materially affect the basic and novel characteristic(s) of the claimed subject matter. Thus, the meaning of the open-ended transitional phrase "comprising" is being defined as encompassing all the specifically recited elements, limitations, steps and/or features as well as any optional, additional unspecified ones. The meaning of the closed-ended transitional phrase "consisting of" is being defined as only including those elements, limitations, steps, integers, and/or features specifically recited in the claim, whereas the meaning of the closed-ended transitional phrase "consisting essentially of" is being defined as only including those elements, limitations, steps, integers, and/or features specifically recited in the claim and those elements, limitations, steps, integers, and/or features that do not materially affect the basic and novel characteristic(s) of the claimed subject matter. Therefore, the open-ended transitional phrase "comprising" (and equivalent open-ended transitional phrases thereof) includes within its meaning, as a limiting case, claimed subject matter specified by the closed-ended transitional phrases "consisting of" or "consisting essentially of." As such, the embodiments described herein or so claimed with the phrase "comprising" expressly and unambiguously provide description, enablement and support for the phrases "consisting essentially of" and "consisting of."

Lastly, the terminology used herein is for the purpose of describing particular embodiments only and is not intended to limit the scope of the present invention, which is defined solely by the claims. Accordingly, the present invention is not limited to that precisely as shown and described.

The invention claimed is:

1. An eye protector for use with an immobilization mask during radiation therapy to reduce radiation exposure to a patient's eye, the eye protector comprising:

a first layer of a compliant material with a concave portion having a concave inner surface and an outer surface opposing the concave inner surface, the concave portion configured to enclose the patient's eye and provide a clearance for the patient's eye when the compliant material is donned atop the patient's eye; and a second layer of a radiation shielding material joined with the first layer and positioned atop the outer surface and substantially covering the concave portion, the radiation shielding material having an inwardly facing surface directed toward the outer surface and an outwardly facing surface directed away from the inwardly facing surface, a majority of the outwardly facing surface having a surface contour configured to be directed obliquely to incident radiation when donned such that at least some of the radiation is reflected away from the patient's eye;

wherein the first layer and the second layer are configured to be donned between the patient's eye and the immobilization mask.

2. The eye protector of claim 1 wherein the surface contour includes one or both of a plurality of dimples and a plurality of concave polyhedrons.

3. The eye protector of claim 1 further comprising a third layer of material positioned atop the second layer, the second layer being sandwiched between the first layer and the third layer.

4. The eye protector of claim 3 wherein the third layer of material is fastened about a perimeter to the second layer enclosing the second layer therebetween.

5. The eye protector of claim 3 wherein the first layer and the third layer of material are each made of a foam laminate material.

6. The eye protector of claim 1 wherein the first layer and the second layer form a right side configured to cover a patient's right eye when donned, a left side is substantially duplicative of the right side construction and is configured to cover a patient's left eye when donned.

7. The eye protector of claim 6 wherein the right side is connected to the left side and is configured to simultaneously cover the patient's right eye and the patient's left eye.

8. The eye protector of claim 7 further comprising a strap connecting the right side and the left side and is configured to wrap about a patient's head when donned.

9. The eye protector of claim 1 wherein the first layer and the second layer form an assembly, the assembly is configured to be sufficiently stiff to resist substantial collapse of the clearance as the immobilization mask is molded about a patient's head, so that the patient's eye can open and close without substantial hindrance caused by contact with the concave inner surface.

10. An eye protector for use with an immobilization mask during radiation therapy to reduce radiation exposure to a patient's right eye and a patient's left eye, the eye protector comprising:

a first layer with a right portion and a left portion, the right portion having a right inner surface and a right outer surface opposing the right inner surface, the left portion having a left inner surface and a left outer surface opposing the left inner surface, the right portion of the first layer configured to substantially cover and to be positioned closest to the patient's right eye and the left portion of the first layer configured to substantially cover and to be positioned closest to the patient's left eye;

a second layer of a radiation shielding material joined with the first layer and positioned atop the outer surface and substantially covering the concave portion, the radiation shielding material having an inwardly facing surface directed toward the outer surface and an outwardly facing surface directed away from the inwardly facing surface; and an assembly comprising the first layer and the second layer, the assembly being configured to be donned between the patient's eye and the immobilization mask and configured to be sufficiently stiff to resist substantial collapse of the right portion and the left portion as the immobilization mask is molded about a patient's head.

11. The eye protector of claim 10 wherein a majority of the outwardly facing surface includes a surface contour configured to be directed obliquely to incident radiation when donned such that at least some of the radiation is reflected away from the patient's eye.

12. The eye protector of claim 11 wherein the surface contour includes one or both of a plurality of dimples and a plurality of concave polyhedrons.

13. The eye protector of claim 10 wherein the right portion further includes a right concave portion and the right inner surface is concave and the left portion further includes a left concave portion and the left inner surface is concave.

14. The eye protector of claim 10 further comprising a third layer of material positioned atop the second layer, the second layer being sandwiched between the first layer and the third layer, and the third layer of material is fastened about a perimeter to the second layer enclosing the second layer therebetween.

15. The eye protector of claim 14 wherein the first layer and the third layer of material are each made of a foam laminate material.

16. The eye protector of claim 10 further comprising a strap connecting the right side and the left side and is configured to wrap about a patient's head when donned.

17. The eye protector of claim 10 wherein the first layer and the second layer form an assembly, the assembly is configured to be sufficiently stiff to resist substantial collapse as the immobilization mask is molded about a patient's head, so that the patient's eye can open and close without substantial hindrance caused by contact with the concave inner surface.

18. A method of fitting an immobilization mask, the method comprising the steps of:

providing an eye protector comprising:

a first layer of material with a concave portion having a concave inner surface and an outer surface opposing the concave inner surface, the concave portion configured to enclose the patient's eye and provide clearance for the patient's eye; and a second layer of a radiation shielding material positioned atop the outer surface of the first layer and substantially covering the concave portion, the radiation shielding material having an inwardly facing surface directed toward the outer surface and an outwardly facing surface directed away from the inwardly facing surface;

positioning the eye protector atop a patient's eye so that each of the patient's eyes are substantially covered by the radiation shielding;

applying the immobilization mask over a patient's head when the immobilization is in a softened state, with the eye protector positioned between the patient's eyes and the immobilization mask;

molding the immobilization mask to conform to the eye protector when the immobilization is in the softened state; and curing the immobilization mask until sufficiently hardened.

19. The method of claim 18 wherein the outwardly facing surface includes a surface contour configured to be directed obliquely to incident radiation when donned such that at least some of the radiation is reflected away from the patient's eye.

20. The method of claim 19 wherein the surface contour includes one or both of a plurality of dimples and a plurality of concave polyhedrons.

\* \* \* \* \*